(12) United States Patent
Kwon et al.

(10) Patent No.: US 11,854,672 B2
(45) Date of Patent: Dec. 26, 2023

(54) METHOD AND APPARATUS FOR GENERATING CHEMICAL STRUCTURE

(71) Applicants: SAMSUNG ELECTRONICS CO., LTD., Suwon-si (KR); RESEARCH & BUSINESS FOUNDATION SUNGKYUNKWAN UNIVERSITY, Suwon-si (KR)

(72) Inventors: Youngchun Kwon, Yongin-si (KR); Seokho Kang, Suwon-si (KR); Won-joon Son, Yongin-si (KR); Dongseon Lee, Yongin-si (KR); Younsuk Choi, Suwon-si (KR)

(73) Assignees: SAMSUNG ELECTRONICS CO., LTD., Suwon-si (KR); RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 674 days.

(21) Appl. No.: 16/897,456

(22) Filed: Jun. 10, 2020

(65) Prior Publication Data

US 2021/0110892 A1    Apr. 15, 2021

Related U.S. Application Data

(60) Provisional application No. 62/913,297, filed on Oct. 10, 2019.

(30) Foreign Application Priority Data

Nov. 19, 2019    (KR) .......................... 10-2019-0149114

(51) Int. Cl.
*G05B 19/4155*    (2006.01)
*G16C 60/00*    (2019.01)
(Continued)

(52) U.S. Cl.
CPC ............. *G16C 60/00* (2019.02); *G16C 20/10* (2019.02); *G16C 20/20* (2019.02); *G16C 20/70* (2019.02)

(58) Field of Classification Search
CPC ........................... G05B 19/4155; G06N 3/084
See application file for complete search history.

(56) References Cited

U.S. PATENT DOCUMENTS 8,126,656 B2     2/2012  Sato et al.
2014/0336807 A1  11/2014  Smith et al.
(Continued)

FOREIGN PATENT DOCUMENTS

JP    5-174109 A    7/1993
JP    4998477 B2    8/2012
(Continued)

*Primary Examiner* — Lam S Nguyen
(74) *Attorney, Agent, or Firm* — Sughrue Mion, PLLC

(57) ABSTRACT

A method and apparatus for generating a new chemical structure using a chemical structure generation model are provided. The method includes receiving a first descriptor of a first chemical structure, encoding the first descriptor into a latent variable using an encoder of the chemical structure generation model, generating a second descriptor by decoding the latent variable using a decoder of the chemical structure generation model, generating the second chemical structure corresponding to the second descriptor.

14 Claims, 10 Drawing Sheets

(51) Int. Cl.
*G16C 20/70* (2019.01)
*G16C 20/10* (2019.01)
*G16C 20/20* (2019.01)

(56) References Cited

U.S. PATENT DOCUMENTS

| 2017/0124482 | A1  | 5/2017  | Yoo et al. |
| 2017/0161635 | A1* | 6/2017  | Oono ................... G06N 3/084 |
| 2018/0032663 | A1  | 2/2018  | Yoo et al. |
| 2020/0401111 | A1* | 12/2020 | Zubarev ............ G05B 19/4155 |

FOREIGN PATENT DOCUMENTS

| JP | 2019-86817 A | 6/2019 |
| KR | 10-2017-0052344 A | 5/2017 |
| KR | 10-2018-0014471 A | 2/2018 |

* cited by examiner

METHOD AND APPARATUS FOR GENERATING CHEMICAL STRUCTURE

CROSS-REFERENCE TO RELATED APPLICATIONS

This application is based on and claims priority under 35 U.S.C. § 119 to U.S. Provisional Patent Application No. 62/913,297, filed on Oct. 10, 2019, in the United States Patent and Trademark Office, and Korean Patent Application No. 10-2019-0149114, filed on Nov. 19, 2019, in the Korean Intellectual Property Office, the disclosures of which are incorporated by reference herein in their entireties.

BACKGROUND

1. Field

The present disclosure relates to a method and apparatus for generating a chemical structure.

2. Description of Related Art

A neural network refers to a computational architecture that models a biological brain. With the advancement of neural network technologies, various types of electronic systems have analyzed input data and extracted valid information using neural networks.

Recently, extensive research has been conducted into methods of selecting chemical structures to be used in material development using the neural network technologies.

When a chemical structure is expressed in the form of a character string or a vector, a three-dimensional (3D) chemical structure is not fully expressed and much information is ignored. Therefore, to overcome the limit of the form of a character string or a vector and to accurately predict properties and generate various chemical structures, techniques for using a 3D chemical structure as input data and output data are desired.

SUMMARY

Provided are a method and apparatus for generating a chemical structure. Also, provided is a non-transitory computer-readable medium having recorded thereon a program for executing the method. The technical problems addressed by the embodiments of the present disclosure are not limited to these as described above.

Additional aspects will be set forth in part in the description which follows and, in part, will be apparent from the description, or may be learned by practice of the presented embodiments of the disclosure.

According to an aspect of the disclosure, a method of generating a second chemical structure using a chemical structure generation model may include receiving a first descriptor of a first chemical structure, encoding the first descriptor into a latent variable using an encoder of the chemical structure generation model, generating a second descriptor by decoding the latent variable using a decoder of the chemical structure generation model, generating the second chemical structure corresponding to the second descriptor.

The method may include inputting the second descriptor into a validity evaluation model; receiving a reward as feedback from the validity evaluation model; and updating the chemical structure generation model based on the reward.

The updating of the chemical structure generation model may include updating a weight of the chemical structure generation model based on the reward for the second descriptor having a first value. The validity evaluation model is configured to output the first value as the reward based on the second descriptor representing a valid chemical structure, and is configured to output a second value as the reward based on the second descriptor representing an invalid chemical structure.

Each of the first descriptor and the second descriptor may have a two-dimensional graph form generated based on vertex information and edge information of a chemical structure.

The updating of the chemical structure generation model may include inputting the second descriptor to a property prediction model; receiving a predicted property value as feedback from the property prediction model; and updating a weight of the chemical structure generation model based on the predicted property value.

The receiving of the reward as the feedback may include determining whether the second descriptor includes a certain structure included in a blacklist; inputting the second descriptor to the validity evaluation model based on determining that the second descriptor does not include the certain structure included in the blacklist; and receiving the reward as the feedback from the validity evaluation model.

The chemical structure generation model may be a conditional variational autoencoder (CVAE) model.

The validity evaluation model may be a reinforcement learning model.

The property prediction model may be a deep neural network model.

According to an aspect of the disclosure, a method of generating a chemical structure using a chemical structure generation model may include obtaining a random latent variable on a latent map of the chemical structure generation model; generating a descriptor by decoding the random latent variable using a decoder of the chemical structure generation model; and generating the chemical structure corresponding to the descriptor.

According to an aspect of the disclosure, an apparatus for generating a second chemical structure using a chemical structure generation model may include a memory configured to store at least one program; and a processor configured to execute the at least one program to encode a first descriptor of a first chemical structure into a latent variable using an encoder of the chemical structure generation model; generate a second descriptor by decoding the latent variable using a decoder of the chemical structure generation model; and generate the second chemical structure corresponding to the second descriptor.

The processor may be configured to input the second descriptor to a validity evaluation model; receive a reward as feedback from the validity evaluation model; and update the chemical structure generation model based on the reward.

The processor may be configured to update a weight of the chemical structure generation model based on the reward for the second descriptor having a first value. The validity evaluation model may be configured to output the first value as the reward based on the second descriptor representing a valid chemical structure, and is configured to output a second value as the reward based on the second descriptor representing an invalid chemical structure.

Each of the first descriptor and the second descriptor may have a two-dimensional graph form generated based on vertex information and edge information of a chemical structure.

The processor may be configured to input the second descriptor to a property prediction model; receive a predicted property value as feedback from the property prediction model; and update a weight of the chemical structure generation model based on the predicted property value.

The processor may be configured to determine whether the second descriptor includes a certain structure included in a blacklist; input the second descriptor into a validity evaluation model based on determining that the second descriptor does not include the certain structure included in the blacklist; and receive the reward as feedback from the validity evaluation model.

According to an aspect of the disclosure, an apparatus for generating a chemical structure using a chemical structure generation model may include a memory configured to store at least one program; and a processor configured to execute the at least one program to obtain a random latent variable on a latent map of the chemical structure generation model; generate a descriptor by decoding the random latent variable using a decoder of the chemical structure generation model; and generate the chemical structure corresponding to the descriptor.

According to an aspect of the disclosure, a non-transitory computer-readable recording medium may have recorded thereon a program that, when executed by a processor, causes the processor to receive a first descriptor of a first chemical structure; encode the first descriptor into a latent variable using an encoder of a chemical structure generation model; generate a second descriptor by decoding the latent variable using a decoder of the chemical structure generation model; and generate a second chemical structure corresponding to the second descriptor.

According to an aspect of the disclosure, a non-transitory computer-readable recording medium may have recorded thereon a program that, when executed by a processor, causes the processor to obtain a random latent variable on a latent map of a chemical structure generation model; generate a descriptor by decoding the random latent variable using a decoder of the chemical structure generation model; and generate a chemical structure corresponding to the descriptor.

According to an aspect of the disclosure, a method may include receiving a first descriptor of a first chemical structure; receiving a target property value; generating, using a chemical structure generation model, a second descriptor of a second chemical structure having the target property value, based on the first descriptor and the target property value; determining that the second chemical structure is a valid chemical structure; determining that the second descriptor is not included in a blacklist; and updating the chemical structure generation model based on determining that the second chemical structure is the valid chemical structure and that the second descriptor is not included in the blacklist.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
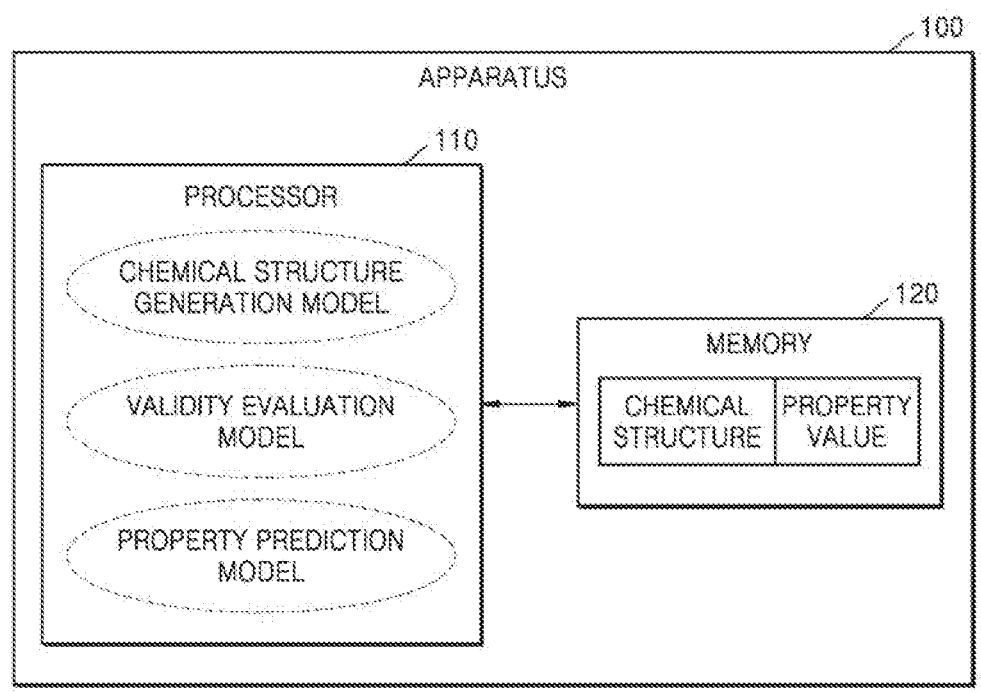
FIG. 1 is a block diagram illustrating a hardware configuration of an apparatus according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

The terms "according to some embodiments" or "according to an embodiment" used throughout the specification do not necessarily indicate the same embodiment.

Some embodiments of the present disclosure may be represented by functional block configurations and various processing operations. Some or all of these functional blocks may be implemented using various numbers of hardware and/or software components that perform particular functions. For example, the functional blocks of the present disclosure may be implemented using one or more microprocessors or circuits for a given function. Also, for example, the functional blocks of the present disclosure may be implemented in various programming or scripting languages. The functional blocks may be implemented with algorithms running on one or more processors. The present disclosure may also employ conventional techniques for electronic configuration, signal processing, and/or data processing. The terms "mechanism," "element," "unit," and "configuration" may be used in a broad sense and are not limited to mechanical and physical configurations.

Also, connection lines or connection members between the components illustrated in the drawings are merely illustrative of functional connections and/or physical or circuit connections. In actual devices, connections between the components may be represented by various functional connections, physical connections, or circuit connections that may be replaced or added.

Hereinafter, embodiments will be described in detail with reference to the accompanying drawings.

FIG. 1 is a block diagram illustrating a hardware configuration of an apparatus 100 according to an embodiment.

The apparatus 100 may be implemented using various types of devices such as a personal computer (PC), a server device, a mobile device, and an embedded device. Examples of the apparatus 100 may include, but are not limited to, a smartphone, a tablet device, an augmented reality (AR) device, an Internet of things (IoT) device, an autonomous vehicle, a robot, a medical device, and the like, which perform speech recognition, image recognition, image classification, and the like, using a neural network. Furthermore, the apparatus 100 may correspond to a dedicated hardware (HW) accelerator mounted on the devices described above. The apparatus 100 may be a hardware accelerator, such as a neural processing unit (NPU), a tensor processing unit (TPU), or a neural engine, which is a dedicated module for driving a neural network, but is not limited thereto.

Referring to FIG. 1, the apparatus 100 includes a processor 110 and a memory 120. FIG. 1 only illustrates components of the apparatus 100 related to the embodiments of the present disclosure. Thus, it is obvious to those skilled in the art that the apparatus 100 may further include any other general-purpose components in addition to the components shown in FIG. 1.

The processor 110 controls the overall function for driving the apparatus 100. For example, the processor 110 controls all operations of the apparatus 100 by executing programs stored in the memory 120 of the apparatus 100. The processor 110 may be implemented as a central processing unit (CPU), a graphics processing unit (GPU), an application processor (AP), or the like, in the apparatus 100, without being limited thereto.

The memory 120 is a hardware component that stores a variety of data processed in the apparatus 100. For example, the memory 120 may store data processed by, or to be processed by, the apparatus 100. The memory 120 may also store applications, drivers, and the like, to be driven by the apparatus 100. The memory 120 may include random access memory (RAM) such as dynamic random access memory (DRAM) or static random access memory (SRAM), read-only memory (ROM), electrically erasable programmable read-only memory (EEPROM), CD-ROM, Blu-ray, or other optical disk storage, a hard disk drive (HDD), a solid state drive (SSD), or flash memory.

The memory 120 stores a chemical structure and a property value, which match each other as one set. The apparatus 100 may read or write a chemical structure and a property value corresponding to the chemical structure from or to the memory 120.

A chemical structure refers to an atomic level structure of a substance. A chemical structure may have a character string (one-dimensional) form in a simple format. For example, a chemical structure may be expressed as simplified molecular-input line-entry system (SMILES) code, smiles arbitrary target specification (SMARTS) code, international chemical identifier (InChi) code, or the like.

A chemical structure may be a structural formula based on the bond between atoms. A chemical structure includes a vertex representing an atom and an edge representing the bond between atoms. In an embodiment, a chemical structure may be expressed in a two-dimensional (2D) graph form.

A property value refers to a characteristic possessed by a substance and may be a real number measured through an experiment or calculated through a simulation. For example, based on a substance being a display material, a property value may be a transmission wavelength, emission wavelength, or the like, with respect to light. Based on a substance being a battery material, a property value may be a voltage. As compared to a descriptor, calculation of a property value may require more complex simulations and time.

The processor 110 may drive a chemical structure generation model, a validity evaluation model, and a property prediction model.

The processor 110 may generate a new chemical structure, which is not previously stored in a database, using the chemical structure generation model. In an embodiment, the chemical structure generation model may be a conditional variational autoencoder (CVAE) model.

In detail, the processor 110 may input a first descriptor of a particular chemical structure to the chemical structure generation model. A descriptor of a chemical structure is high-dimensional data. An encoder of the chemical structure generation model may encode a descriptor into a low-dimensional latent variable, and a decoder of the chemical structure generation model may decode the latent variable, thereby outputting a high-dimensional second descriptor. Based on the first descriptor input to the chemical structure generation model being different from the second descriptor output from the chemical structure generation model, a chemical structure corresponding to the second descriptor may be a new chemical structure.

In addition, the processor 110 may determine a valid chemical structure and an invalid chemical structure using the validity evaluation model. In an embodiment, the validity evaluation model may be a reinforcement learning model.

In detail, the processor 110 may input a descriptor of a new chemical structure generated from the chemical structure generation model to the validity evaluation model. In an embodiment, the validity evaluation model may identify the syntax of the descriptor of the new chemical structure using a library and determine whether the new chemical structure is valid. For example, the library may be an Rdkit library but is not limited thereto.

The validity evaluation model may output different rewards according to whether the new chemical structure is valid. A reward output from the validity evaluation model may be used to update the decoder of the chemical structure generation model.

Also, the processor 110 may predict a property value of a new chemical structure using the property prediction model. In an embodiment, the property prediction model may be a deep neural network model. In detail, the processor 110 may input a descriptor of a chemical structure to the property prediction model. The property prediction model may output a property value based on the descriptor input thereto.

The apparatus 100 may further include a user interface (not shown). The user interface refers to a unit used to input data for controlling the apparatus 100. Examples of the user interface may include, but are not limited to, a key pad, a dome switch, a touch pad (e.g., a capacitive overlay type, a resistive overlay type, an infrared beam type, a surface acoustic wave type, an integral strain gauge type, a piezo electric type, or the like), a jog wheel, and a jog switch.

Hereinafter, methods of generating a chemical structure by using the apparatus 100 and evaluating the generated chemical structure will be described in detail. The methods to be described below may be performed by the processor 110 and the memory 120 of the apparatus 100.

Figure 2:
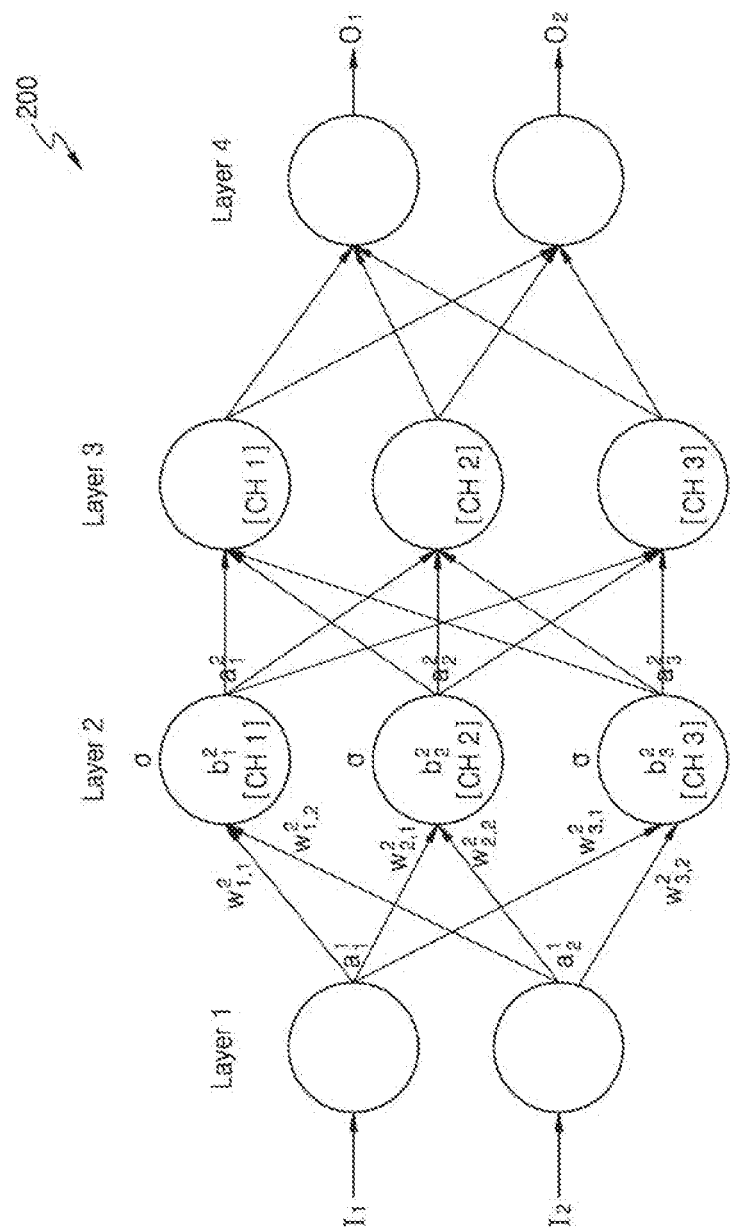
FIG. 2 is a diagram for describing a computation performed by a deep neural network according to an embodiment.

FIG. 2 is a diagram for describing a computation performed by a deep neural network 200 according to an embodiment.

Referring to FIG. 2, the deep neural network 200 may have a structure including an input layer, hidden layers, and an output layer. The deep neural network 220 may perform a computation based on received input data (e.g., $I_1$ and $I_2$), and generate output data (e.g., $O_1$ and $O_2$) based on a computation result.

For example, as illustrated in FIG. 2, the deep neural network 200 may include an input layer (Layer 1), two hidden layers (Layer 2 and Layer 3), and an output layer (Layer 4). Because the deep neural network 200 may include many layers to process valid information, the deep neural network 200 may process more complex data as compared to a neural network including a single layer. Although the deep neural network 200 illustrated in FIG. 2 includes 4 layers, the deep neural network 200 may also include more or fewer layers and more or fewer channels than those illustrated therein. That is, the deep neural network 200 may have various structures of layers different from that illustrated in FIG. 2.

Each of the layers included in the deep neural network 200 may have a plurality of channels. The channels may correspond to a plurality of artificial nodes known as neurons, processing elements (PEs), units, or the like. For example, as illustrated in FIG. 2, Layer 1 may include two channels (nodes), and Layers 2 and 3 may each include three channels. However, each of the layers included in the deep neural network 200 may have various numbers of channels (nodes).

The channels included in each of the layers of the deep neural network 200 may be interconnected to process data. For example, a channel may perform a computation of data received from channels of one layer, and output a computation result to channels of another layer.

Input and output of each channel may be referred to as input activation and output activation. That is, an activation may be an output of one channel, or a parameter corresponding to an input of channels included in a successive layer. Each of the channels may determine an activation thereof based on activations and weights received from channels included in a previous layer. The weight is a parameter used to calculate the output activation of each channel and may be a value assigned to the relationship between channels.

Each of the channels may be processed by a computational unit or a processing element that receives an input and outputs an output activation. The input-output of each channel may be mapped. For example, when σ is an activation function, $w_{j,k}^i$ is a weight from a k-th channel included in an (i−1)-th layer to a j-th channel included in an i-th layer, $b_j^i$ is a bias of the j-th channel included in the i-th layer, and $a_k^{i-1}$ an activation of the j-th channel of the i-th layer, an activation $a_j^i$ may be calculated using Expression 1 below.

$$a_j^i = \sigma(\Sigma_k(w_{j,k}^i \times a_k^{i-1}) + b_j^i)$$  Expression 1

As illustrated in FIG. 2, an activation of a first channel CH1 of a second layer, i.e., Layer 2, may be expressed as $a_1^2$. In addition, $a_1^2$ may have a value of $a_1^2 = \sigma(w_{1,1}^2 \times a_1^1 + w_{1,2}^2 \times a_2^1 + b_1^2)$ according to Expression 1. However, Expression 1 described above is an example for describing the activation and the weight used to process data in the deep neural network 200 and the embodiment is not limited thereto. The activation may be a value obtained by inputting the sum of activations received from the previous layer to an activation function and processing the result with a rectified linear unit (ReLU).

In an embodiment, the deep neural network 200 may determine a factor defining the relationship between a descriptor and a property via learning using descriptors and property values. That is, among Layers 1 to 4 constituting the deep neural network 200, the descriptor corresponds to the input layer (Layer 1), the property value corresponds to the output layer (Layer 4), and the factor corresponds to at least one hidden layer (Layer 2 and/or Layer 3).

The deep neural network 200 may perform a computation on a descriptor of a chemical structure received in an input layer and may output a property value in an output layer.

Figure 3A:
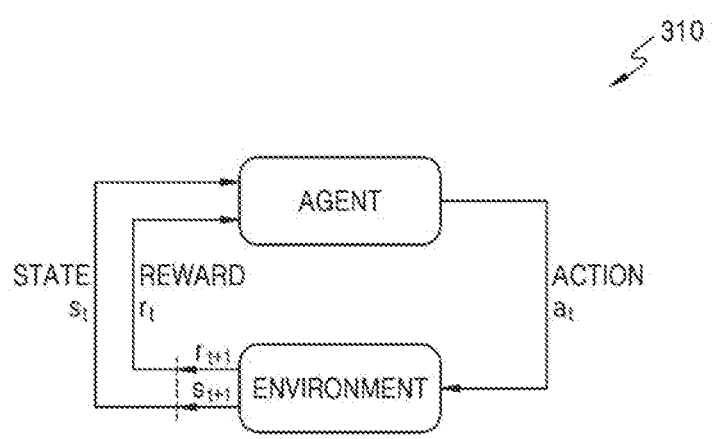
FIGS. 3A and 3B are diagrams for describing reinforcement learning and deep reinforcement learning (DRL), according to an embodiment.
Figure 3B:
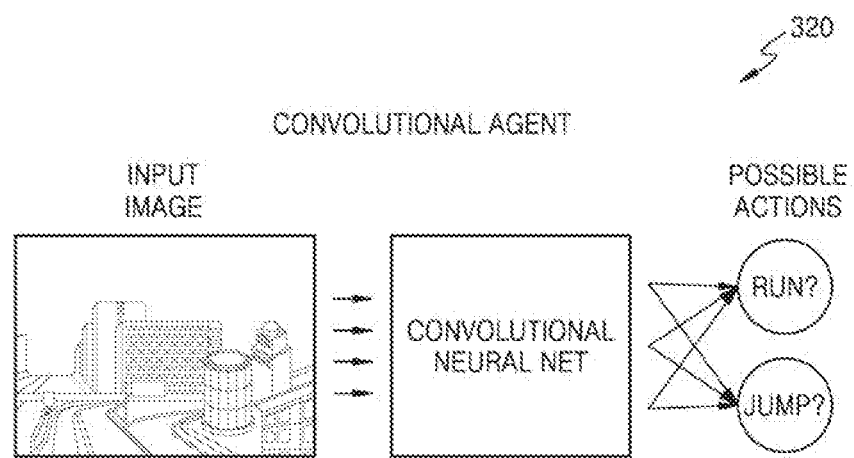

FIGS. 3A and 3B are diagrams for describing reinforcement learning and deep reinforcement learning (DRL), according to an embodiment.

Referring to FIG. 3A, a reinforcement learning model 310 may include elements such as an agent, a state, an environment, an action, and a reward.

An agent refers to an entity which performs actions. An action refers to any moves that an agent can make. A state is an agent's concrete and immediate situation perceived by the agent. An environment receives an agent's current state and action and outputs a reward and a next state. A reward is a feedback by which the success or failure of an agent's action is measured.

A policy is a strategy that an agent employs to determine a next action based on a current state. An agent chooses an action that may give the highest reward in a certain state.

Q-value refers to an expected reward for policy π in a current state. $Q^\pi(s, a)$ refers to a long-term return of an action "a" in a current state "s" based on the action "a" being taken under the policy π. Q-value maps state-action pairs to rewards.

The reinforcement learning model 310 refers to an algorithm by which an agent determines a policy defined by a series of actions maximizing the cumulative reward.

Referring to FIG. 3B, a DRL model 320 is an agent that learns a method of mapping state-action pairs to rewards.

Similar to other deep neural network models, the DRL model 320 also uses correlation coefficients to approximate the function relating inputs to outputs. The DRL model 320 performs learning to find a a more accurate correlation coefficient or weight by iteratively adjusting the weight along a gradient to produce less error.

In the DRL model 320, a convolutional network may be used to recognize an agent's state. The convolutional network of the DRL model 320 determines the rank of actions that can be performed by an agent in a current state.

The DRL model 320 may adjust weights and improve the interpretation of state-action pairs using the difference between expected reward and ground-truth reward based on feedback from an environment.

Figure 4:
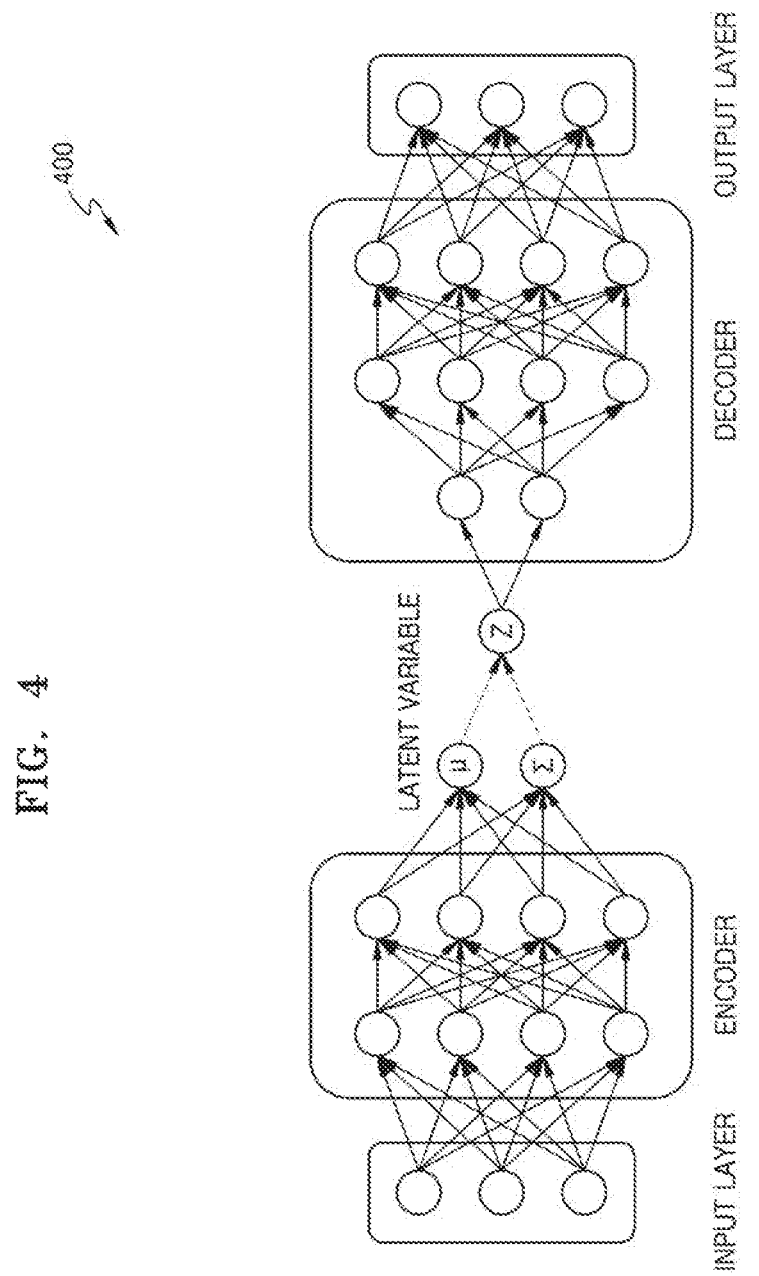
FIG. 4 is a diagram for describing a computation performed by a conditional variational autoencoder (CVAE) according to an embodiment.

FIG. 4 is a diagram for describing a computation performed by a CVAE 400 according to an embodiment.

Referring to FIG. 4, the CVAE 400 has a structure that includes an input layer, an encoder, a decoder, and an output layer. High-dimensional data is used as input data to the input layer of the CVAE 400, and the encoder performs encoding of converting the high-dimensional data into a low-dimensional latent variable "z". In an embodiment, the latent variable "z" follows a normal distribution with a mean μ and a variance σ, and may be two-dimensional to fifty-dimensional data. The decoder decodes the low-dimensional latent variable "z" such that new high-dimensional data that is not present in a database may be output from the output layer.

The latent variable "z" may be mapped to a latent map. Based on a predetermined value z' included in a region of the latent map, to which the latent variable z is not mapped, being input to and decoded by the decoder, new data that is not in the database may be generated in the output layer. Alternatively, based on the latent variable "z" being input to and decoded by the decoder, new data that is not in the database may be generated in the output layer according to the trained level of the decoder.

The first descriptor of the particular chemical structure may be input to the input layer of the CVAE 400. A descriptor of a chemical structure is high-dimensional data. The encoder may encode the descriptor into a low-dimensional latent variable, and the decoder of the chemical structure generation model may decode the latent variable, thereby outputting a high-dimensional second descriptor. Based on the first descriptor input to the chemical structure generation model being different from the second descriptor output from the chemical structure generation model, a chemical structure corresponding to the second descriptor may be a new chemical structure.

Figure 5:
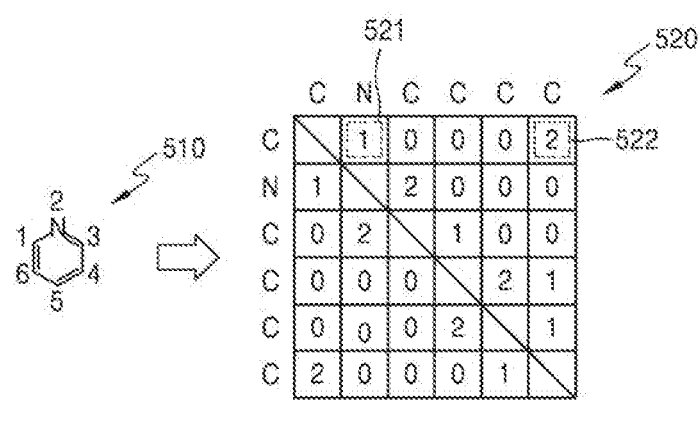
FIG. 5 is a diagram for describing a descriptor in the form of a two-dimensional (2D) graph, according to an embodiment.

FIG. 5 is a diagram for describing a descriptor in the form of a 2D graph, according to an embodiment.

Referring to FIG. 5, a chemical structure 510 may include a vertex representing an atom and an edge representing the bond between atoms. A descriptor of the chemical structure 510 may have a 2D graph form 520, which is generated based on vertex information and edge information.

In detail, vertex information may be a one-hot vector for each of the atoms forming a chemical structure. For example, a one-hot vector for a carbon atom, C, of the chemical structure 510 may be "00010", and a one-hot vector for a nitrogen atom, N, of the chemical structure 510 may be "00001".

Edge information may be bond information between adjacent atoms in a chemical structure. For example, since carbon corresponding to vertex number 1 and nitrogen corresponding to vertex number 2 are involved in a single bond, a first cell 521 has a value of 1. Because carbon corresponding to vertex number 1 and carbon corresponding to vertex number 6 are involved in a double bond, a second cell 522 has a value of 2.

In an embodiment, a descriptor of a chemical structure, which is used as input/output data in a chemical structure generation model, a validity evaluation model, and a property prediction model, may have the 2D graph form 520.

Figure 6:
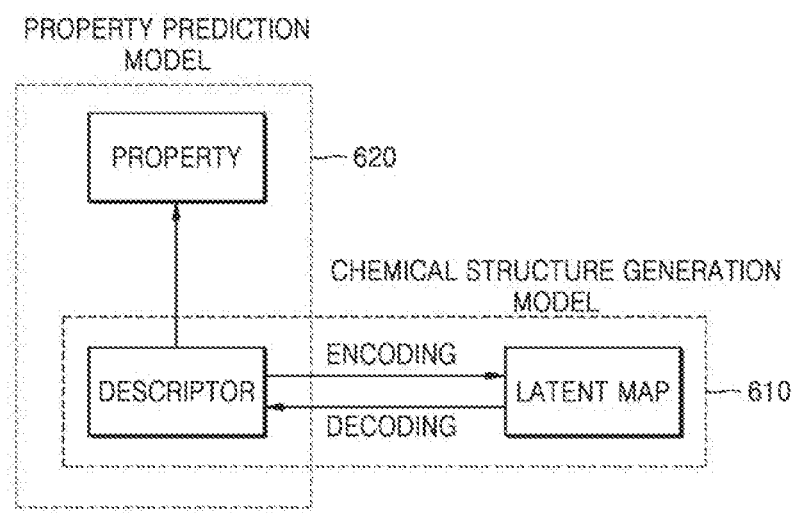
FIG. 6 is a conceptual diagram for describing a process of generating a chemical structure and predicting a property, according to an embodiment.

FIG. 6 is a conceptual diagram for describing a process of generating a chemical structure and predicting a property, according to an embodiment.

FIG. 6 illustrates a property prediction model 620 and a chemical structure generation model 610.

A descriptor used as input data in the chemical structure generation model 610 and the property prediction model 620 may have a character string (one-dimensional) form in a simple format. For example, a chemical structure may be expressed as SMILES code, SMARTS code, InChi code, or the like. For example, a structural formula may be expressed as SMILES code as shown in Expression 2 or as SMARTS code as shown in Expression 3.

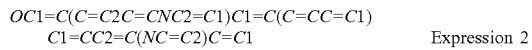

OC1=C(C=C2C=CNC2=C1)C1=C(C=CC=C1)
C1=CC2=C(NC=C2)C=C1        Expression 2

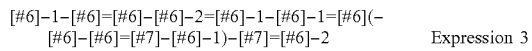

[#6]-1-[#6]=[#6]-[#6]-2=[#6]-1-[#6]-1=[#6](-
[#6]-[#6]=[#7]-[#6]-1)-[#7]=[#6]-2        Expression 3

Alternatively, a descriptor may be a structural formula based on the bond between atoms. In an embodiment, a descriptor may be expressed in a 2D graph form, which is generated based on vertex information and edge information. A descriptor of a 2D graph form has been described with reference to FIG. 5 above, and thus, detailed descriptions thereof will be omitted.

A descriptor of a particular chemical structure may be input to the chemical structure generation model 610. The descriptor may be encoded into a latent variable, and the latent variable may be mapped to a latent map. In an embodiment, a latent map is visualizable coordinates to which a 2D latent variable is mapped. Because latent variables gather according to a structure type in a latent map, similarity between the latent variables may be visualized and identified using the latent map.

A latent variable mapped to a latent map may be decoded and output as a descriptor. A descriptor input to the chemical structure generation model 610 may be different from a descriptor output from the chemical structure generation model 610. Based on an input descriptor being different from an output descriptor, an input chemical structure is different from an output chemical structure.

A descriptor output from the chemical structure generation model 610 may be input to the property prediction model 620. Based on a descriptor input to the chemical structure generation model 610 being different from a descriptor output from the chemical structure generation model 610, the property prediction model 620 may output a property value of a new chemical structure, which is different from the particular chemical structure, by using, as input data, the descriptor output from the chemical structure generation model 610.

Figure 7:
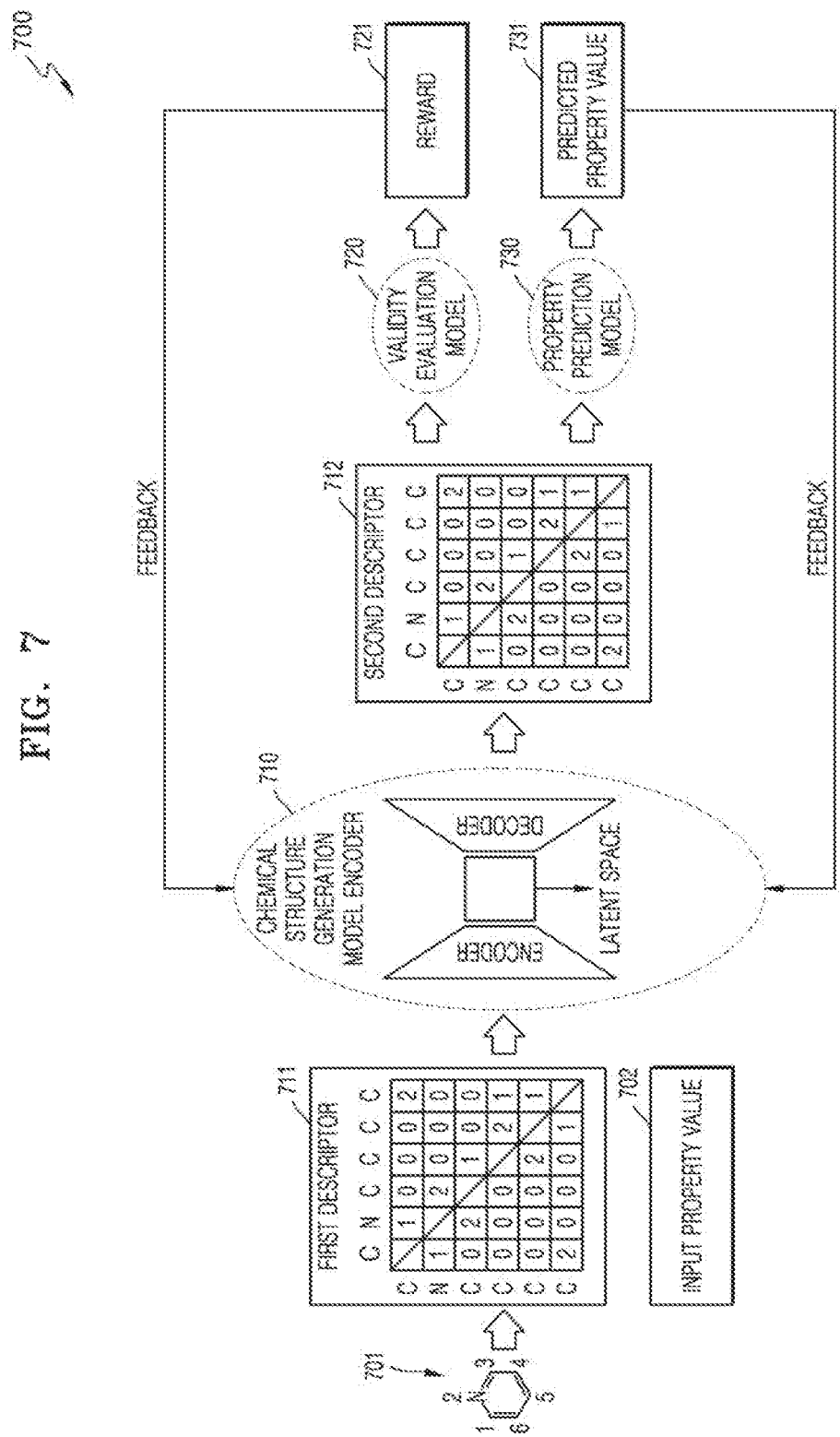
FIG. 7 is a diagram for describing a process of training a chemical structure generation model, according to an embodiment.

FIG. 7 is a diagram for describing a process of training a chemical structure generation model, according to an embodiment.

An apparatus 700 for training a chemical structure may include a chemical structure generation model 710, a validity evaluation model 720, and a property prediction model 730. Although it is illustrated in FIG. 7 that the chemical structure generation model 710, the validity evaluation model 720, and the property prediction model 730 are included in one apparatus 700, at least part of any one of the chemical structure generation model 710, the validity evaluation model 720, and the property prediction model 730 may be mounted on another independent apparatus.

The chemical structure generation model 710 may generate a new chemical structure that is not previously stored in a database. In an embodiment, the chemical structure generation model 710 may be a CVAE model.

In detail, the chemical structure generation model 710 may receive a first descriptor 711 of a chemical structure 701 as input. The first descriptor 711 is high-dimensional data. The chemical structure generation model 710 may encode the first descriptor 711 into a low-dimensional latent variable using an encoder. The chemical structure generation model 710 may also output a second descriptor 712, which is high-dimensional, by decoding the latent variable using a decoder.

As shown in FIG. 7, the first descriptor 711 and the second descriptor 712 may have a 2D graph form, which is generated based on vertex information and edge information of the chemical structure 701.

The first descriptor 711 input to the chemical structure generation model 710 may be different from or the same as the second descriptor 712 output from the chemical structure generation model 710. Based on the first descriptor 711 being different from the second descriptor 712, a chemical structure corresponding to the second descriptor 712 may be a new chemical structure that is not previously stored in a database. Hereinafter, it is assumed that the first descriptor 711 is different from the second descriptor 712.

The validity evaluation model 720 may determine a valid chemical structure and an invalid chemical structure. A valid chemical structure may refer to a chemical structure that may exist in the real world. For example, each of the atoms included in a chemical structure is bonded to an adjacent atom in a limited way according to the number of electrons. The validity evaluation model 720 may determine a chemical structure satisfying the limitation to be valid. However, a method by which the validity evaluation model 720 determines the validity of a chemical structure is not limited thereto. In an embodiment, the validity evaluation model 720 may be a reinforcement learning model.

The validity evaluation model 720 may receive the second descriptor 712 output from the chemical structure generation model 710 as an input. The validity evaluation model 720 may output a reward 721 based on the second descriptor 712.

In detail, based on the second descriptor 712 representing a valid chemical structure, the validity evaluation model 720 may output a first value as the reward 721. Alternatively, based on the second descriptor 712 representing an invalid chemical structure, the validity evaluation model 720 may output a second value as the reward 721. For example, the first value may be "1" and the second value may be "2".

The chemical structure generation model 710 may receive the reward 721 output from the validity evaluation model 720 as feedback, and determine whether to update the weight thereof based on the reward 721.

In an embodiment, the chemical structure generation model 710 may be trained by updating the weight thereof based on the reward 721 received from the validity evaluation model 720 being the first value. In other words, the chemical structure generation model 710 may update the weight thereof based on the second descriptor 712 representing a valid chemical structure, and may refrain from updating the weight thereof based on the second descriptor 712 representing an invalid chemical structure.

In an embodiment, the training efficiency of the chemical structure generation model 710 may be increased by training the chemical structure generation model 710 using only descriptors that represent valid chemical structures.

The second descriptor 712 output from the chemical structure generation model 710 through the above-described process may be used as input data of the property prediction model 730. The property prediction model 730 may predict a property value of a new chemical structure. In an embodiment, the property prediction model 730 may be a deep neural network model. In detail, the property prediction model 730 may receive the second descriptor 712 as input and perform an operation on the second descriptor 712, thereby outputting a predicted property value 731 for the second descriptor 712.

The chemical structure generation model 710 may receive the predicted property value 731 output from the property prediction model 730 as feedback and determine whether to update the weight thereof based on the predicted property value 731.

In an embodiment, the chemical structure generation model 710 may be trained by updating the weight thereof based on the predicted property value 731 received from the property prediction model 730 being equal to or greater than a target property value. In other words, in an embodiment, the training efficiency of the chemical structure generation model 710 may be increased by training the chemical structure generation model 710 using descriptors that represent chemical structures having the predicted property value 731 that is equal to or greater than a target property value.

In an embodiment, the apparatus 700 may further include a blacklist verification model (not shown). The blacklist refers to a list of partial structures that are unfavorable to synthesis and performance (e.g., blacklisted structures). A chemical structure has a property value for a particular property (e.g., a transmission wavelength or an emission wavelength). The chemical structure generation model 710 may generate a new chemical structure that has a property value matching a target property value (e.g., an emission wavelength $\lambda=350$ nm). At this time, based on a partial structure corresponding to a blacklisted structure included in the blacklist being included in the new chemical structure, the probability of the property value of the new chemical structure not matching the target property value increases.

For example, the blacklist may be include parameters such as "inclusion of a ring structure having at most four angles," "at least six zeros," "inclusion of other atoms than C, O, and N," "inclusion of a ring structure having at least seven angles," or the like. However, the blacklist is not limited to the above examples and may vary with desired synthesis and performance.

The blacklist verification model may receive the second descriptor 712 output from the chemical structure generation model 710 as input. The blacklist verification model may determine whether the second descriptor 712 includes a certain structure included in the blacklist.

Based on the blacklist verification model determining that the second descriptor 712 does not include the certain structure included in the blacklist, the blacklist verification model may transmit the second descriptor 712 to the validity evaluation model 720. In other words, in an embodiment, descriptors including the certain structures included in the blacklist are excluded from the training of the chemical structure generation model 710, and accordingly, the training efficiency of the chemical structure generation model 710 may be increased.

Figure 8:
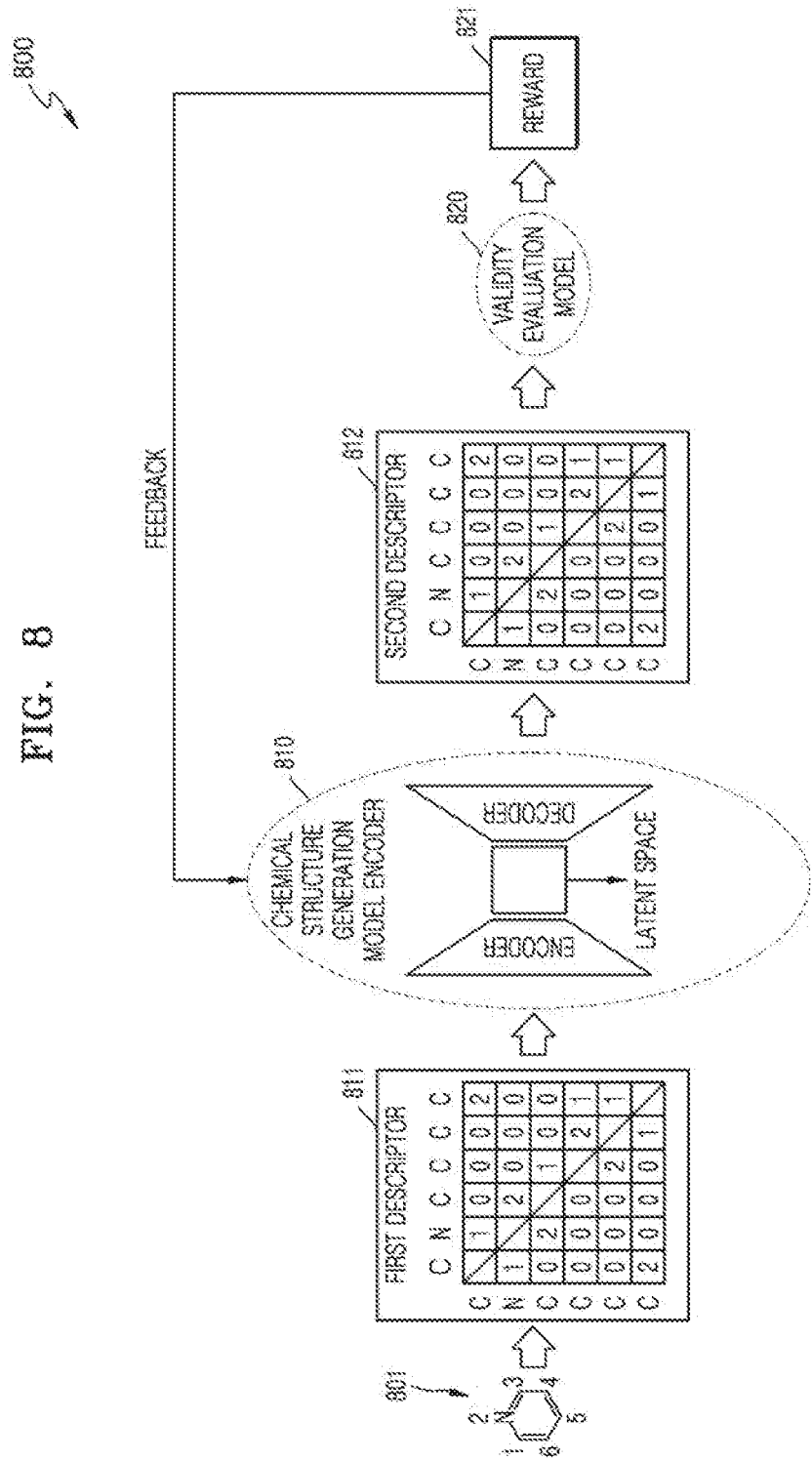
FIG. 8 is a diagram for describing a process of generating a new chemical structure using a chemical structure generation model, according to an embodiment.

FIG. 8 is a diagram for describing a process of generating a new chemical structure using a chemical structure generation model, according to an embodiment.

Referring to FIG. 8, an apparatus 800 for generating a chemical structure may include a chemical structure generation model 810. The chemical structure generation model 810 may be a model that has been trained through the processes described with reference to FIG. 7. The chemical structure generation model 810 may generate a new chemical structure that is not previously stored in a database. In an embodiment, the chemical structure generation model 810 may be a CVAE model.

In an embodiment, the chemical structure generation model 810 may receive a first descriptor 811 of a chemical structure 801 as input. The first descriptor 811 is high-dimensional data. The chemical structure generation model 810 may encode the first descriptor 811 into a low-dimensional latent variable using an encoder. The chemical structure generation model 810 may output a second descriptor 812, which is high-dimensional, by decoding the low-dimensional latent variable using a decoder.

The first descriptor 811 input to the chemical structure generation model 810 may be different from or the same as the second descriptor 812 output from the chemical structure generation model 810. Based on the first descriptor 811 being different from the second descriptor 812, a chemical structure corresponding to the second descriptor 812 may be a new chemical structure that is not previously stored in a database.

In an embodiment, the apparatus 800 may obtain a random latent variable on a latent map of the chemical structure generation model 810. Latent variables having a similar structure gather on the latent map. Based on a new chemical structure having a particular structure being generated, the apparatus 800 may obtain a random latent variable in a region, in which latent variables having the particular structure gather on the latent map. The apparatus 800 may generate a new chemical structure by decoding the ransom latent variable using the decoder.

The chemical structure generation model 810 may have received, as feedback, a reward from the validity evaluation model 720 described with reference to FIG. 7 and may have been trained, and therefore, a new valid chemical structure may be generated using the chemical structure generation model 810.

The chemical structure generation model 810 may also receive a reward from the validity evaluation model 720 as feedback during an inference process such that a weight of the chemical structure generation model 810 may be updated.

A validity evaluation model 820 may receive the second descriptor 812 output from the chemical structure generation model 810 as input. The validity evaluation model 820 may output a reward 821 based on the second descriptor 812.

Based on the second descriptor 812 representing a valid chemical structure, the validity evaluation model 820 may output a first value as the reward 821. Alternatively, based on the second descriptor 812 representing an invalid chemical structure, the validity evaluation model 820 may output a second value as the reward 821.

The chemical structure generation model 810 may receive the reward 821 output from the validity evaluation model 820 as feedback, and determine whether to update the weight thereof based on the reward 821.

In an embodiment, the chemical structure generation model 810 may update the weight thereof based on the reward 821 received from the validity evaluation model 820 having the first value. In other words, the chemical structure generation model 810 may update the weight thereof based on the second descriptor 812 representing a valid chemical structure; and may refrain from updating the weight thereof based on the second descriptor 812 representing an invalid chemical structure.

In an embodiment, the weight of the chemical structure generation model 810 is updated using the validity evaluation model 820 during an inference process as well as a training process, and accordingly, the inference efficiency of the chemical structure generation model 810 may be increased.

In addition, at least one selected from the property prediction model 730 and the blacklist verification model, which have been described above with reference to FIG. 7, may be used during the inference process of the chemical structure generation model 810, thereby increasing the inference efficiency of the chemical structure generation model 810.

Figure 9:
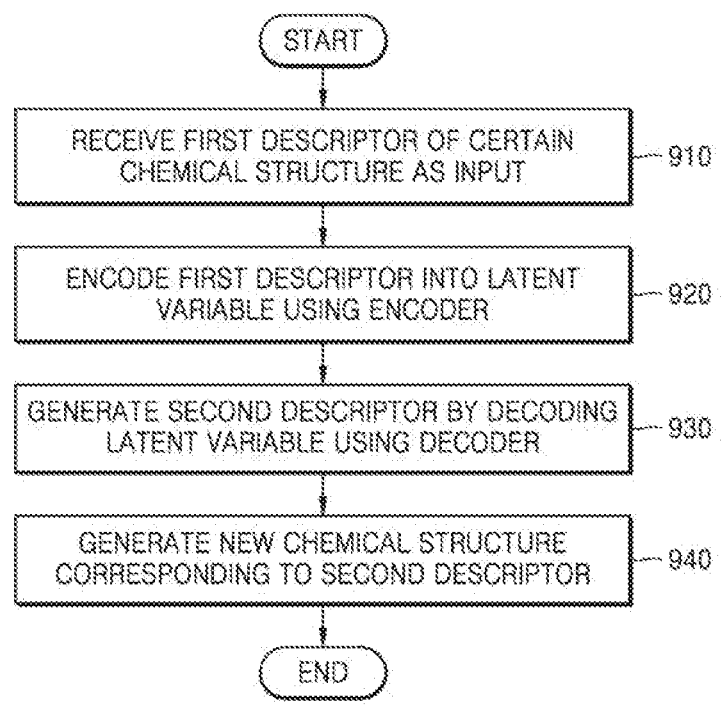
FIG. 9 is a flowchart of a method of generating a chemical structure using a chemical structure generation model, according to an embodiment.

FIG. 9 is a flowchart of a method of generating a chemical structure using a chemical structure generation model, according to an embodiment. The method of FIG. 9 is related to the embodiments described above with reference to the drawings. Thus, although omitted in the following description, the content described above with reference to the drawings may also be applied to the method of FIG. 9.

Referring to FIG. 9, a chemical structure generation model may receive a first descriptor of a certain chemical structure as input in operation 910.

The chemical structure generation model may be a CVAE model including an encoder and a decoder.

In an embodiment, descriptors (e.g., a first descriptor and a second descriptor) may have a 2D graph form. In detail, descriptors may have a 2D graph form that is generated based on vertex information and edge information of a chemical structure.

The vertex information may be a one-hot vector for each of the atoms forming a chemical structure, and the edge information may be bond information between adjacent atoms in the chemical structure.

The chemical structure generation model may encode the first descriptor into a latent variable using the encoder in operation 920.

The chemical structure generation model may encode the high-dimensional first descriptor into the low-dimensional latent variable using the encoder. The latent variable may be mapped to a latent map. In an embodiment, the latent map includes visualizable coordinates to which a 2D latent variable is mapped. Because latent variables gather according to a structure type in a latent map, similarity between the latent variables may be visualized and identified using the latent map.

The chemical structure generation model may generate a second descriptor by decoding the latent variable using the decoder in operation 930.

The chemical structure generation model may output the high-dimensional second descriptor by decoding the latent variable using the decoder.

The first descriptor input to the chemical structure generation model may be different from the second descriptor output from the chemical structure generation model. Based on the first descriptor being different from the second descriptor, an input chemical structure may be different from an output chemical structure. Based on the first descriptor being different from the second descriptor, a chemical structure corresponding to the second descriptor may be a new chemical structure that is not previously stored in a database.

The chemical structure generation model may generate a new chemical structure corresponding to the second descriptor in operation 940.

Based on the second descriptor being different from the first descriptor, which is input to the chemical structure generation model in operation 910, the chemical structure generation model may generate a new chemical structure that is not in the database.

Parameters included in the chemical structure generation model may be updated during an inference process using the chemical structure generation model. In an embodiment, during an inference processing using the chemical structure generation model, the parameters of the chemical structure generation model may be updated through reinforcement learning.

In detail, the chemical structure generation model may input the second descriptor to a validity evaluation model, and receive a reward from the validity evaluation model as feedback. The validity evaluation model may determine a valid chemical structure and an invalid chemical structure. The validity evaluation model may be a reinforcement learning model.

For example, based on the second descriptor representing a valid chemical structure, the chemical structure generation model may receive a reward corresponding to a first value from the validity evaluation model as feedback. Alternatively, based on the second descriptor representing an invalid chemical structure, the chemical structure generation model may receive a reward corresponding to a second value from the validity evaluation model as feedback.

The chemical structure generation model may also update the weight thereof based on the reward.

The chemical structure generation model may update the weight thereof based on the second descriptor received from the validity evaluation model representing a valid chemical structure; and may refrain from updating the weight thereof based on the second descriptor representing an invalid chemical structure.

In detail, the chemical structure generation model may update the weight thereof based on the reward received from the validity evaluation model having the first value; and may refrain from updating the weight thereof based on the reward received from the validity evaluation model having the second value. In other words, the chemical structure generation model may be trained by updating the weight thereof based on the reward received from the validity evaluation model having the first value.

In an embodiment, the parameters of the chemical structure generation model are updated using descriptors representing a valid chemical structure, and therefore, the training and inference efficiencies of the chemical structure generation model may be increased.

In an embodiment, the chemical structure generation model may input the second descriptor to a property prediction model, and receive a predicted property value from the property prediction model as feedback. The property prediction model may be a deep neural network model. The chemical structure generation model may update the weight thereof based on the predicted property value.

In detail, the chemical structure generation model may update the weight thereof based on the predicted property value received from the property prediction model being equal to or greater than a target property value. In other words, in an embodiment, the parameters of the chemical structure generation model are updated using descriptors representing a chemical structure having the predicted property value that is equal to or greater than the target property value, and therefore, the training and inference efficiencies of the chemical structure generation model may be increased.

In an embodiment, the chemical structure generation model may determine whether the second descriptor includes a certain structure included in a blacklist. The chemical structure generation model may transmit the second descriptor to the validity evaluation model based on the chemical structure generation model determining that the second descriptor does not include the certain structures included in the blacklist. In other words, in an embodiment, descriptors including certain structures included in the blacklist are excluded from the updating of the parameters of the chemical structure generation model, and therefore, the training and inference efficiencies of the chemical structure generation model may be increased.

The aforementioned embodiments may be implemented by a non-transitory computer-readable medium including instructions executable by a computer, such as a program module, executed by a computer. The non-transitory computer-readable medium may be any recording medium that may be accessed by a computer and may include volatile and non-volatile media and removable and non-removable media. Also, the non-transitory computer-readable medium may include computer storage media and communication media. The computer storage media may include volatile and non-volatile and removable and non-removable media implemented using any method or technology to store information such as computer-readable instructions, data structures, program modules, or other data. The communication media may include computer-readable instructions, data structures, program modules, or other data in a modulated data signal, or other transport mechanisms and include any type of delivery media.

In addition, throughout the specification, the term "unit" may refer to a hardware component such as a processor or a circuit and/or a software component executed by the hardware component such as a processor.

According to the embodiments, a chemical structure generation model is trained using descriptors that represent a valid chemical structure, and therefore, the training and inference efficiencies of the chemical structure generation model may be increased.

It should be understood that embodiments described herein should be considered in a descriptive sense and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A method of generating a second chemical structure using a chemical structure generation model, the method comprising:
　receiving a first descriptor of a first chemical structure;
　encoding the first descriptor into a latent variable using an encoder of the chemical structure generation model;
　generating a second descriptor by decoding the latent variable using a decoder of the chemical structure generation model;
　generating the second chemical structure corresponding to the second descriptor;
　determining whether the second chemical structure corresponds to a valid chemical structure; and
　based on determining that the second chemical structure corresponds to a valid chemical structure, updating the chemical structure generation model based on the second descriptor,
　wherein updating the chemical structure generation model based on the second descriptor comprises:
　　inputting the second descriptor into a validity evaluation model, wherein the validity evaluation model is configured to:
　　　output a first value as a reward based on the second descriptor representing a valid chemical structure, and
　　　output a second value as the reward based on the second descriptor representing an invalid chemical structure; and
　　updating a weight of the chemical structure generation model based on the reward for the second descriptor having the first value.

2. The method of claim 1, wherein determining whether the second chemical structure corresponds to a valid chemical structure comprises:
　receiving the reward as feedback from the validity evaluation model.

3. The method of claim 2, wherein the updating of the chemical structure generation model comprises:

inputting the second descriptor to a property prediction model;
receiving a predicted property value as feedback from the property prediction model; and
updating a weight of the chemical structure generation model based on the predicted property value.

4. The method of claim 3, wherein the property prediction model is a deep neural network model.

5. The method of claim 2, wherein the receiving of the reward as the feedback comprises:
determining whether the second descriptor includes a certain structure included in a blacklist;
inputting the second descriptor to the validity evaluation model based on determining that the second descriptor does not include the certain structure included in the blacklist; and
receiving the reward as the feedback from the validity evaluation model.

6. The method of claim 2, wherein the validity evaluation model is a reinforcement learning model.

7. The method of claim 1, wherein each of the first descriptor and the second descriptor has a two-dimensional graph form generated based on vertex information and edge information of a chemical structure.

8. The method of claim 1, wherein the chemical structure generation model is a conditional variational autoencoder (CVAE) model.

9. An apparatus for generating a second chemical structure using a chemical structure generation model, the apparatus comprising:
a memory configured to store at least one program; and
a processor configured to execute the at least one program to:
encode a first descriptor of a first chemical structure into a latent variable using an encoder of the chemical structure generation model;
generate a second descriptor by decoding the latent variable using a decoder of the chemical structure generation model;
generate the second chemical structure corresponding to the second descriptor;
determine whether the second chemical structure corresponds to a valid chemical structure; and
based on determining that the second chemical structure corresponds to a valid chemical structure, update the chemical structure generation model based on the second descriptor,
wherein the processor is configured to execute the at least one program to update the chemical structure generation model based on the second descriptor by:
inputting the second descriptor into a validity evaluation model, wherein the validity evaluation model is configured to:
output a first value as a reward based on the second descriptor representing a valid chemical structure, and
output a second value as the reward based on the second descriptor representing an invalid chemical structure; and
updating a weight of the chemical structure generation model based on the reward for the second descriptor having the first value.

10. The apparatus of claim 9, wherein the processor is further configured to determine whether the second chemical structure corresponds to a valid chemical structure by:
receiving the reward as feedback from the validity evaluation model.

11. The apparatus of claim 9, wherein each of the first descriptor and the second descriptor has a two-dimensional graph form generated based on vertex information and edge information of a chemical structure.

12. The apparatus of claim 9, wherein the processor is further configured to:
input the second descriptor to a property prediction model;
receive a predicted property value as feedback from the property prediction model; and
update a weight of the chemical structure generation model based on the predicted property value.

13. The apparatus of claim 9, wherein the processor is further configured to:
determine whether the second descriptor includes a certain structure included in a blacklist;
input the second descriptor into a validity evaluation model based on determining that the second descriptor does not include the certain structure included in the blacklist; and
receive the reward as feedback from the validity evaluation model.

14. A non-transitory computer-readable recording medium having recorded thereon a program that, when executed by a processor, causes the processor to:
receive a first descriptor of a first chemical structure;
encode the first descriptor into a latent variable using an encoder of a chemical structure generation model;
generate a second descriptor by decoding the latent variable using a decoder of the chemical structure generation model;
generate a second chemical structure corresponding to the second descriptor;
determine whether the second chemical structure corresponds to a valid chemical structure; and
based on determining that the second chemical structure corresponds to a valid chemical structure, update the chemical structure generation model based on the second descriptor,
wherein instructions, when executed by the processor, cause the processor to update the chemical structure generation model based on the second descriptor by:
inputting the second descriptor into a validity evaluation model, wherein the validity evaluation model is configured to:
output a first value as a reward based on the second descriptor representing a valid chemical structure, and
output a second value as the reward based on the second descriptor representing an invalid chemical structure; and
updating a weight of the chemical structure generation model based on the reward for the second descriptor having the first value.

* * * * *